United States Patent [19]

Chaundy et al.

[11] Patent Number: 5,153,177
[45] Date of Patent: * Oct. 6, 1992

[54] PROCESS FOR INCORPORATING A MATERIAL IN A CROSSLINKED GELATIN, AND PRODUCT THEREFROM

[75] Inventors: Frederick K. Chaundy, Grosse Ile; David K. Bower, Wyandotte; Terence K. Kilbride, Jr., Bloomfield Hills, all of Mich.

[73] Assignee: BASF Corporation, Parsippany, N.J.

[*] Notice: The portion of the term of this patent subsequent to Jun. 30, 2009 has been disclaimed.

[21] Appl. No.: 639,646

[22] Filed: Jan. 10, 1991

[51] Int. Cl.$^5$ .................. C07K 3/28; C07K 15/20; A61K 37/12; A23L 1/0562
[52] U.S. Cl. .................. 514/21; 426/576; 530/354; 530/395; 530/410; 530/411
[58] Field of Search .......... 530/354, 410, 411, 355; 514/21; 426/576

[56] References Cited

U.S. PATENT DOCUMENTS

| | | | |
|---|---|---|---|
| 2,196,146 | 4/1940 | Collins | 530/354 |
| 3,899,598 | 8/1975 | Fischer et al. | 426/576 |
| 3,904,771 | 9/1975 | Donnelly et al. | 426/576 |
| 4,407,836 | 10/1983 | Bosco et al. | 426/576 |
| 4,500,453 | 2/1985 | Shank | 530/354 |
| 4,615,896 | 10/1986 | Brown et al. | 426/576 |
| 4,670,247 | 6/1987 | Scialpi | 424/484 |

Primary Examiner—Merrell C. Cashion, Jr.
Assistant Examiner—Andrew G. Rozycki

[57] ABSTRACT

A method of crosslinking protein comprises making a composition which comprises a protein, a sugar, a water-soluble salt of a carboxylic acid, water, and an additional ingredient which is to be encapsulated or entrapped within the crosslinked protein matrix. The composition is thereafter heated while maintaining the moisture content at a level of at least about 3 weight percent, based on the weight of the composition.

A product comprises a protein which is crosslinked to degree at which it is substantially insoluble upon being placed in water at 100° C. for at least 3 minutes, a sugar, a water-soluble salt of a carboxylic acid, water, and an additional ingredient which is encapsulated or entrapped within the crosslinked protein matrix.

19 Claims, No Drawings

PROCESS FOR INCORPORATING A MATERIAL IN A CROSSLINKED GELATIN, AND PRODUCT THEREFROM

BACKGROUND OF THE INVENTION

The present invention relates in general to the field of crosslinking protein, especially gelatin. The crosslinking of protein (and especially gelatin) is a well developed field in which many different means of crosslinking have been proposed. More specifically, the present invention pertains to incorporating materials in the crosslinked gelatin.

The process of the present invention requires the use of a selected sugar (or sugars), a selected salt (or salts) and at least a minimal amount of water, and, of course, at least one additional ingredient which is to be encapsulated. Never before the present invention has there been provided any process for crosslinking of protein with these ingredients. This particular combination of ingredients permits the crosslinking to be performed at temperatures previously inoperable to obtain the desired degree of crosslinking with ingredients that are safe for both food and animal feed applications. This "low temperature advantage" is very important because it permits crosslinking to be performed in the presence of the many heat sensitive materials (which of course have been present during the crosslinking process) without substantial thermal degradation thereof.

Thus the present invention is applicable to a wide range of arts, such as food sciences, photographic sciences, pharmaceuticals, etc, i.e. wherever protein crosslinking is utilized in combination with any additional chemical species which may be thermally sensitive, as well as in all situations in which it is advantageous to conserve energy. The invention is particularly useful in the vitamin arts, especially vitamin A, which undergoes thermal degradation at the temperatures previously required for obtaining substantial protein crosslinking with commonly used food ingredients. Thus the process of the present invention is particularly valuable for crosslinking protein (especially gelatin) in the presence of temperature-sensitive ingredients, such as vitamins, without substantial thermal degradation of the temperature sensitive ingredient as well as without requiring the use of a toxic crosslinking agent such as formaldehyde. As stated above, the advantages of the process of the present invention are especially important with respect to producing gelatin-encapsulated vitamin A products. Gelatin and sugar are commonly used food and feed ingredients and the salt may be one which is "generally recognized as safe" (i.e. "GRAS"). Thus one is able to use the process of the present invention to obtain a vitamin A encapsulated in a crosslinked gelatin wherein the process is carried out at a temperature at which there is no substantial thermal degradation of the vitamin A.

U.S. Pat. No. 2,196,146 describes subject matter which is related to the present invention. The '146 patent relates to improved food products and process for making the same, and particularly to food products containing sugar and acid, such as those commonly known as gelatin desserts that generally are marketed in the form of a dry powder and usually comprise gelatin. Among the acids mentioned in the '146 patent are "fruit acids" (such as tartaric acid), and to the additional use of salts of organic acids such as acetates. The '146 patent repeatedly refers to the "setting" of the gelatin.

In contrast to the '146 patent, the present invention requires that the protein be "crosslinked". Crosslinking differs from "setting" in that crosslinking is irreversible whereas setting (also known as "gelation") is reversible. The process of setting involves the transformation of a solution to a gel. The addition of heat to the gel can then be used to melt the gel so that a solution is formed. In stark contrast, crosslinking involves an irreversible chemical reaction, in that the addition of heat to the crosslinked protein will not result in transforming the crosslinked protein into a solution of the protein.

Another related patent of which applicants are aware is U.S. Pat. No. 4,500,453, issued to Shank. This patent relates to crosslinked collagen-derived protein compositions having improved Bloom gel strength and increased viscosity. Furthermore, the '453 patent relates to a process for crosslinking the protein with an aluminum salt of acetic acid selected from the group consisting of aluminum subacetate, aluminum triacetate and an alkali metal aluminum acetate double salt. The '453 patent requires the use of an aluminum salt, as can be seen from the comparative example therein (Example 2) which shows that the substitution of a sodium salt for the aluminum salt renders the process of the '453 patent inoperable.

In contrast, the present invention differs from the '453 patent in that the process of the present invention requires the use of at least one of a group of sugars. If one were to alter the process of the present invention by carrying it out in the absence of at least one of these sugars, the required degree of crosslinking will not result. Note Example 2 herein, which proves that upon using, for example, calcium acetate as the salt, the process of the present invention is inoperable (no crosslinking occurs) in the absence of at least one of the group of sugars. In stark contrast, '453 patent nowhere mentions the use of any sugar, not to mention one or more of the group of sugars which are used in the process of the present invention.

U.S. Pat. No. 4,670,247, issued to Scialpi, refers to a process for the preparation of fat-soluble vitamin active beadlet compositions which exhibit stability when exposed to the feed pelleting process. The process includes forming an aqueous emulsion of a fat-soluble vitamin-active material, gelatin, and a sugar, converting the emulsion to dry particulate form containing the non-aqueous constituents of the emulsion, and heat treating the resulting product to form water insoluble beadlets.

In contrast to the '247 patent, the process of the present invention requires the use of at least one of a group of salts. The '247 nowhere refers to either mandatory use of (or even optional use of) any salt whatsoever. Note Example 2 herein, which prove that at a preferred temperature (75° C. for the production of encapsulated vitamin A) for the process of the present invention, inoperability results in the absence of at least one of the group of salts specified.

BRIEF DESCRIPTION OF THE INVENTION

The present invention relates to both a process for making a crosslinked protein, as well as to a crosslinked proteinaceous product. In general, the process of the present invention is carried out by first making an aqueous composition which comprises:
(1) a protein, (2) a sugar which is at least one member selected from the group consisting of fructose, and glucose, (3) a salt which is at least one member selected from the group consisting of water-soluble salts of carboxylic acids, sodium carbonate, potassium carbonate, calcium sulfate, and calcium phosphate, (4) water, and (5) an additional ingredient.

The aqueous composition is then heated while the moisture content of the composition is maintained at a level of at least about 3 weight percent. Both the making of the composition (i.e. the selection and proportioning of the ingredients) as well as the heating of the composition, are to be carried out so that the protein is crosslinked to a degree at which it is substantially water insoluble upon being placed in boiling water (i.e. water at 100° C.) for at least three minutes.

In general, the product of the present invention comprises:

A. a protein wherein the protein is crosslinked to a degree at which it is substantially water insoluble upon being placed in water at 100° C. for at least 3 minutes;

B. a sugar, wherein the sugar is at least one member selected from the group consisting of fructose, and glucose;

C. a salt which is at least one member selected from the group consisting of water-soluble salts of carboxylic acids, sodium carbonate, potassium carbonate, calcium sulfate, and calcium phosphate;

D. water;

E. an additional ingredient.

It is an object of the present invention to provide a process for crosslinking a protein (especially gelatin) in the presence of an additional ingredient, with the crosslinking reaction utilizing a sugar and a GRAS salt.

It is a further object of the present invention to crosslink gelatin to a degree of insolubility in boiling water for at least three minutes, without elevating the gelatin to a temperature which causes the degradation of an additional ingredient which is present during the crosslinking reaction.

It is a further object of the present invention to provide a process for crosslinking gelatin to a degree of insolubility in boiling water for at least three minutes, the crosslinking taking place at a temperature below 90° C., the crosslinking taking place in the presence of a fat-soluble vitamin product.

It is a further object of the present invention to provide a process for crosslinking gelatin utilizing a GRAS salt, a sugar, and water, while heating the gelatin to a temperature of from about 55° C. to about 85° C., wherein the heating is maintained for a period of from about 2 hours to about 24 hours, in the presence of an additional ingredient.

It is a further object of the present invention to provide a crosslinked vitamin product comprising gelatin which has been crosslinked to a degree that it is insoluble in boiling water at 100° C. for at least 3 minutes, a sugar, a GRAS salt, water, and an additional ingredient which is substantially encapsulated within the crosslinked gelatin.

It is a further object of the present invention to provide a crosslinked vitamin product comprising gelatin which has been crosslinked to a degree that it is insoluble in boiling water at 100° C. for at least 3 minutes, and a heat-sensitive ingredient within the crosslinked gelatin matrix, wherein the heat sensitive ingredient is a fat-soluble vitamin.

DETAILED DESCRIPTION OF THE PREFERRED EMBODIMENTS

A primary objective of the process of the present invention is to prepare a substantially crosslinked, water-insoluble protein matrix. A substantially crosslinked, water-insoluble protein matrix is defined as a matrix which is substantially insoluble after 3 minutes in boiling water.

The phrases "crosslinked protein" and "crosslinked gelatin", as commonly used, pertain to a wide spectrum of products having widely differing degrees of crosslinking. The effects of the crosslinking range from a mere increase in the viscosity of the product, to the formation of a very rigid and brittle product which is of course completely insoluble in water. In the field of encapsulating vitamins, pharmaceuticals, food additives, etc, it is desirable to crosslink a protein (especially gelatin) to a degree that the resulting crosslinked matrix is substantially insoluble in boiling water for at least three minutes. If less than this amount of crosslinking is achieved, the encapsulated product will frequently escape during subsequent processing (e.g. pelleting or extusion), resulting in undesirable degradation, etc. of the encapsulated product.

Crosslinking is to be distinguished from gelation in that gelation is the result of hydrogen bonding between individual polymer molecules to form an infinite, 3-dimensional network whereas crosslinking is the result of a chemical reaction between polymer molecules. If polymer molecules are permitted to crosslink to a certain degree, the result is that the crosslinking reaction is irreversible. In contrast, gelation is reversible by merely heating the gel above its melting point.

Heating will generally not reverse a crosslinking reaction. However, reversal of a crosslinking reaction may occur, at least to some degree, if the crosslinking reaction is so slight that the crosslinked bonds between polymer molecules are not strong enough to withstand, for example, thermal stress, such as that from boiling water. For the purposes of encapsulation of vitamins, pharmaceuticals, food additives, flavors, fragrances, photographic additives, etc. in proteins, it is desirable to crosslink the polymer to a degree that it is insoluble when placed in boiling water for at least 3 minutes. This level of gelatin crosslinking has surprisingly been found to be achievable with a sugar and a GRAS salt upon heating to relatively low temperatures (e.g. 55° C. to 85° C.) at which certain heat-sensitive ingredients (e.g. vitamin A) are not substantially degraded.

The preferred salt for use in the crosslinking process and product of the present invention is a salt which is categorized as "generally recognized as safe" (i.e. GRAS). GRAS has been defined by the United States Food and Drug Administration in parts 182, 184, and 582 of 21 Code of Federal Regulations (21 CFR).

The process of the present invention involves making a composition which comprises a protein, among other ingredients, followed by heating the composition in order to crosslink the protein. The term "composition", as used herein, is meant to require that the combined ingredients are mixed to a degree of substantial uniformity. The composition can be a solution, an emulsion, or a gel. Preferably the composition is a gelled emulsion.

The composition comprises a protein, a sugar, a salt, water, and an additional ingredient which is to be encapsulated or entrapped within a crosslinked protein matrix. The protein is preferably gelatin. However, while the gelatin may, in general, have a bloom value of from about 0 to about 300, the gelatin preferably has a bloom value of from about 50 to about 300. It is believed that whereas vitamin supplements used in animal feeds typically utilize gelatin having a bloom value of about 85 (i.e. from about 80 bloom to about 90 bloom), food additives usually utilize gelatin having a bloom value of from about 200 to about 300 and pharmaceuticals utilize all bloom values. Furthermore, the gelatin may be either a Type A or a Type B gelatin. Type A gelatin is obtained from acid processing of collogen. Type B gelatin is obtained from alkaline processing of collogen.

The composition is made by dissolving the protein, the sugar, and the salt (and possibly even the additional ingredient, depending upon its solubility in water) in water. In the event that the protein is gelatin, this require that the gelatin and water be heated to about 60° C. in order to completely dissolve the gelatin.

In general, the protein is present in the composition in an amount of from about 10 weight percent to about 70 weight percent, based on the weight of the composition. Still more preferably the gelatin is present in the composition in a amount of from about 10 weight percent to about 30 weight percent, based on the weight of the composition. Most preferably the protein is present in the composition in an amount of about 17 weight percent, based on the weight of the composition.

Preferably the protein is gelatin. Preferably the gelatin has a bloom of from about 50 to about 300. Most preferably the gelatin has a bloom value of about 85 if the product of the process is to be utilized as a vitamin supplement for animal feed.

The composition further comprises a sugar. As with the protein, the sugar is also dissolved in water in making the composition. In general, the sugar is at least one member selected from the group consisting of fructose, and glucose. The term fructose is meant to include not simply pure fructose, but also high fructose corn syrup, isomers of fructose, as well as fructose-bearing mixtures such as invert sugar (a mixture of fructose and glucose). The term glucose is meant to include not simply pure glucose, but also isomers of glucose (such as mannose) as well as glucose-bearing mixtures such as high glucose corn syrup. Most preferably the sugar is high fructose corn syrup.

In general, the sugar is present in the compostion in an amount of from about 3 weight percent to about 30 weight percent, based on the weight of the compostion. Preferably the sugar is present in the composition in an amount of from about 5 weight percent to about 20 weight percent, based on the weight of the composition. Most preferably the sugar is present in an amount of about 10 weight percent, based on the weight of the composition.

The composition further comprises a water-soluble salt of a carboxylic acid as well as other water soluble salts. More specifically, the water-soluble salt is at least one member selected from the group consisting of sodium acetate, calcium acetate, sodium propionate, calcium propionate, sodium benzoate, sodium carbonate, potassium carbonate, calcium sulfate, calcium phosphate, aluminum subacetate, sodium tartrate, and sodium glutarate. Preferably the salt is at least one member selected from the group consisting of sodium acetate, calcium acetate, sodium propionate, calcium propionate, sodium benzoate, sodium carbonate, and potassium carbonate. Most preferably the salt is sodium acetate.

In general, the salt is present in the composition in an amount of from about 0.5 weight percent to about 25 weight percent, based on the weight of the composition. Preferably the salt is present in the composition in an amount of from about 1 weight percent to about 10 weight percent, based on the weight of the composition. Most preferably the salt is present in the composition in an amount of about 2 weight percent, based upon the weight of the composition.

The composition further comprises water. The water content of the composition is considerably greater before the heating step than after the heating step, because the initial water content of the composition must be high enough to dissolve the protein (gelatin), sugar, salt, and possibly even the additional ingredient(s) (if they are water soluble). However, once the ingredients are dissolved, the composition is most preferably allowed to gel, and thereafter the gel is preferably dried to a moisture content of from about 1 weight percent to about 3 weight percent, before the heating step is initiated. Most preferably, the moisture content is about 7 weight percent.

Upon first making the composition, the water is present in an amount which is great enough to at least dissolve all of the protein (gelatin), sugar, and salt present in the composition. In general, the water (i.e. moisture) content of the composition is from about 3 weight percent to about 90 weight percent, based on the weight of the composition. Preferably the moisture content of the composition is from about 25 weight percent to about 60 weight percent, based on the weight of the composition. Most preferably the moisture content of the composition is about 48 weight percent.

After the gelatin, sugar, and salt are dissolved, during the heating step the moisture content may be reduced to a level down to as low as about 3 weight percent, based on the total (reduced) weight of the composition. It has been found that the crosslinking reaction can be carried out at relatively low temperatures so long as the moisture content of the composition being heated is at least about 3 weight percent. Most preferably the moisture content of the composition is about 7 weight percent during the heating step.

The composition further comprises an additional ingredient. Of course, the additional ingredient should be compatible with the composition. The phrase "compatible with the composition" means that the additional ingredient does not undergo some undesirable reaction with the salt, sugar, protein, etc. As examples of "incompatiblity", the additional ingredient should not modify the protein so that the protein will not thereafter undergo crosslinking so that a water insoluble protein matrix cannot be formed. The additional ingredient should not be so volatile that it completely boils off of the composition at the temperatures required to keep the protein dissolved (e.g. 60° C.), and the additional ingredient should not react with the protein, salt, or sugar so that any one of them are rendered insoluble under the conditions for carrying out the process of the present invention.

Examples of additional ingredients which may be used in the present invention include: vitamins, pharmaceuticals, flavors, fragrances, food additives, photographic additives, etc. There are thousands of possible additional ingredients for use in the present invention. The additional ingredient may be either encapsulated within the crosslinked protein matrix, or may be simply entrapped within the crosslinked protein matrix. If the additional ingredient is insoluble in the aqueous composition, and an emulsion is formed before the heating step, the result will be an additional ingredient which is encapsulated within the crosslinked protein matrix. If the additional ingredient is soluble in the aqueous composition, the result will be an additional ingredient which is entrapped within the crosslinked protein matrix.

Preferred additional ingredients are vitamins. Still more preferred additional ingredients are fat-soluble vitamins, which are of course not substantially water soluble. The fat-soluble vitamins, when combined with the aqueous composition, are preferably thereafter agitated so that an emulsion is formed.

A most preferred additional ingredient is vitamin A oil. Since vitamin A oil is substantially insoluble in the aqueous composition, emulsification can be used to produce an encapsulated vitamin A product in which a crosslinked gelatin matrix is insoluble when placed in boiling water for at least three minutes. This is a very desirable result since the encapsulated vitamin A product can be utilized in feed formulations which are subjected to the harsh conditions (high temperature, high moisture, high pressure, and high shear) found in pelleting and extrusion processes. Just as importantly, the present invention enables this relatively high degree of crosslinking without subjecting the vitamin A oil to a temperature at which substantial degradation of the vitamin occurs. Vitamin A oil is particularly sensitive to heat, the vitamin A degrading substantially when heated at temperatures of 90° C. for even relatively short periods of time (e.g. 4 hours). Heating the vitamin A oil to 120° C. for a period of even just 12 minutes results in significant degradation of the vitamin. Even relatively small amounts of degradation of the vitamin A oil (e.g. 5% degradation) result in significant loss of value, since the cost of the vitamin A oil is so much greater than the cost of the other ingredients (i.e. the gelatin, sugar, and salt) utilized in the formulation.

In general, the additional ingredient may be present in the composition in an amount of from about 0.1 weight percent to about 60 weight percent, based on the weight of the composition before the heating (or drying) step. Preferably the additional ingredient is present in an amount of from about 5 weight percent to about 55 weight percent. Most preferably the additional ingredient is present in an amount of from about 22 weight percent.

Once the composition is made by combining the protein, sugar, salt, water, and additional ingredient, the composition is then heated in order to crosslink the protein. The heating step is carried out in order to crosslink the protein to a degree at which it is substantially insoluble upon being placed in boiling water (i.e. at 100° C.) for at least 3 minutes. Still more preferably the protein (preferably gelatin) is crosslinked to a degree that it is substantially insoluble in boiling water for at least 15 minutes.

Throughout that period of the heating step during which the crosslinking reaction is taking place, it has been found necessary to keep the moisture content of the composition at a level of at least about 3 weight percent, based on the total weight of the composition. In general, during the heating step the moisture content of the compostion may be within the range of from about 3 weight percent up to about 90 weight percent. However, it has been found that the maximum amount of water which can be present during the crosslinking reaction varies depending upon the particular salt utilized. It has been found that if sodium carbonate is utilized as the salt, the water content may be at least as high as 60 weight percent, based on the total weight of the composition (see Example 11, infra). However, if the salt utilized is sodium acetate, the maximum amount of water which can be present during the crosslinking reaction is about 30 weight percent water. For most of the salts which can be used in the present invention, the maximum amount of moisture at which the crosslinking reaction will occur is about 30 weight percent.

In general, the heating may be carried out at any temperature desired and for any period of time desired, so long as the protein is crosslinked to a degree that it is insoluble in boiling water for at least three minutes. If gelatin is the protein utilized in the composition, the temperature range to be utilized may be from about 55° C. to about 180° C. However, if a heat-sensitive additional ingredient is present during the crosslinking step (i.e. an ingredient such as vitamin A, which begins to degrade at appreciable rates at temperatures around 90° C.), it is preferable to carry out the heating step within a temperature range of from about 55° C. to about 85° C. Most preferably the heating step is carried out at a temperature of about 75° C.

The duration of the heating step is quite broad, depending upon the temperature employed in the process. If a relatively high temperature is employed (e.g. around 180° C.), the heating step need be no longer than about 30 seconds to a few minutes in order to produce the desired degree of crosslinking. However, if a high temperature is used (i.e. a temperature of at least about 100° C.), the composition is preferably a gel having a moisture content of less than about 10 percent, by weight. If a relatively low temperature is employed (e.g. from around 55° C. to around 80° C.), the heating step may be carried out for a period of several hours (e.g. from about 2 hours to about 24 hours) in order to produce the desired degree of crosslinking.

A moisture content of at least 3 weight percent has been found to be necessary in order to sustain the crosslinking reaction. Thus, it is necessary to maintain this moisture level during that portion of the heating step that the crosslinking reaction is to progress. Further heating after the moisture content has dropped below 3 weight percent will not sustain further crosslinking of the protein, and is also undesirable if a heat-sensitive ingredient is present in the composition. As a general rule, the heating step should be carried out at a temperature below that at which any heat-sensitive ingredient degrades, and as a general rule the heating step should be no longer than that period required to produce the desired degree of crosslinking.

The present invention also relates to a crosslinked protein product which encapsulates (or entraps) an additional ingredient. In general, the product of the present invention comprises:

A. a protein which is crosslinked to a degree at which it is substantially insoluble upon being placed in boiling water for at least 3 minutes;

B. a sugar wherein the sugar is at least one member selected from the group consisting of fructose and glucose;

C. a salt wherein the salt is at least one member selected from the group consisting of water-soluble salts of carboxylic acids, sodium carbonate, potassium carbonate, calcium sulfate, and calcium phosphate;
D. water; and
E. an additional ingredient.

The crosslinked protein in the product of the present invention is a protein as may be produced by the above-described process of the present invention. The protein is preferably gelatin, and is preferably a gelatin having a bloom of from about 50 to about 300. The gelatin most preferably has a bloom of about 85 (i.e. a bloom of from about 80 to about 90). The protein is crosslinked to a degree at which it is substantially insoluble upon being placed in boiling water for at least 3 minutes.

In general, the crosslinked protein is present in the product in an amount of from about 10 weight percent to about 70 weight percent, based on the weight of the product. Preferably the crosslinked protein is present in an amount of from about 15 weight percent to about 50 weight percent, based on the weight of the product. Most preferably the protein is present in an amount of about 30 weight percent, based on the weight of the product.

The sugar in the product of the present invention is a sugar as is described above with reference to the process of the present invention. Generally, the sugar of the present invention is at least one member selected from the group consisting of fructose and glucose. These terms are again used as is described above with reference to the process of the present invention. Most preferably the sugar is high fructose corn syrup.

In general, the sugar is present in the product in an amount of from about 3 weight percent to about 30 weight percent, based on the weight of the product. Preferably the sugar is present in the product in an amount of from about 10 weight percent to about 30 weight percent, based on the weight of the product. Most preferably the sugar is present in an amount of about 20 weight percent, based on the weight of the product.

The product further comprises a water-soluble salt. More specifically, the water-soluble salt is at least one member selected from the group consisting of sodium acetate, calcium acetate, sodium propionate, calcium propionate, sodium benzoate, sodium carbonate, potassium carbonate, calcium sulfate, calcium phosphate, aluminum subacetate, sodium tartrate, and sodium glutarate. Preferably the salt is at least one member selected from the group consisting of sodium acetate, calcium acetate, sodium propionate, calcium propionate, sodium benzoate, sodium carbonate, and potassium carbonate. Most preferably the salt is sodium acetate.

In general, the water soluble salt is present in the product in an amount of from about 0.5 weight percent to about 25 weight percent, based on the weight of the product. Preferably the salt is present in the product in an amount of from about 2 weight percent to about 10 weight percent, based on the weight of the product. Most preferably the salt is present in the product in an amount of about 5 weight percent, based upon the weight of the product.

The product further comprises water. In general, water is present in the product in an amount of from about 1 weight percent to about 18 weight percent, based on the weight of the product. Preferably water is present in an amount of from about 3 weight percent to about 13 weight percent, and most preferably water is present in an amount of about 4 weight percent, based on the weight of the product. If a vitamin particulate is made according to a most preferred embodiment of the invention (see Example 3, infra), it is most preferred that the product is dried to a moisture content of about 4 weight percent, based on the weight of the product.

The product further comprises an additional ingredient. Examples of additional ingredients which may be used in the present invention include: vitamins, pharmaceuticals, flavors, fragrances, food additives, photographic additives, etc. There are thousands of possible additional ingredients for use in the present invention. The additional ingredient may be either encapsulated within the crosslinked protein matrix, or may be simply entrapped within the crosslinked protein matrix. If the additional ingredient is insoluble in water, the product will comprise an additional ingredient which is encapsulated within the crosslinked protein matrix. If the additional ingredient is soluble in the aqueous composition, the product will comprise an additional ingredient which is entrapped within the crosslinked protein matrix.

The additional ingredient may be a water-soluble vitamin. The water-soluble vitamin will be entrapped within the crosslinked protein matrix. The water-soluble vitamin may be at least one member selected from the group consisting of vitamin C, thiamine, pyridoxine, riboflavin, biotin, nicotinamide, folic acid, cobalamin, and pantothenic acid.

More preferably the additional ingredient is a fat-soluble vitamin which is at least one member selected from the group consisting of vitamin A, carotinoids, vitamin D, vitamin E, and vitamin K. The fat-soluble vitamin is encapsulated within the crosslinked protein (preferably gelatin) matrix. The most preferred additional ingredient is vitamin A oil.

The additional ingredient may comprise both fat-soluble as well as water-soluble vitamins.

Small quantities of other ingredients including antioxidants, butylated hydroxy anisole (BHA), butylated hydroxy toluene (BHT), ethoxyquin (6-ethoxy-1,2-dihydro-2,2,4-trimethyl-quinoline), and the like; and humectants, such as glycerin, sorbitol, polyethylene glycol, and the like; emulsifiers, such as lecithin; extenders and solubilizers; coloring agents; and complexing agents; can also be incorporated into the composition made in the process and product of the present invention.

In general, the additional ingredient may be present in the product in an amount of from about 0.1 weight percent to about 60 weight percent, based on the weight of the product. Preferably the additional ingredient is present in an amount of from about 10 weight percent to about 50 weight percent. Most preferably the additional ingredient is present in an amount of from about 40 weight percent.

EXAMPLES

Example 1

Preparation of Gelatin Slabs

The gelatin compositions described in the examples below were prepared by dissolving gelatin and other ingredients in water at 60° C., then allowing the resulting solutions to set, or gel, at ambient temperature, into slabs approximately 1 to 2 millimeters in thickness and approximately 75 millimeters in diameter. The gelled slabs were then allowed to dry at ambient temperature and humidity for about 16-20 hours, with a final moisture content of about 25 weight percent (based on the weight of the slab).

Example 2

Three solutions (solutions A, B and C) were prepared. Each solution contained 18.6 parts by weight Type B gelatin having a bloom value of from about 80 to about 90 dissolved in 50.2 parts (by weight) water heated at 60° C. to dissolve the gelatin. Additionally, solution A contained fructose (3 parts), solution B contained calcium acetate (3 parts), and solution C contained calcium acetate (3 parts) and fructose (3 parts).

Two slabs were prepared from each solution, via the procedure described in Example 1, supra. One slab from each solution was placed in an oven at 70° C. for 6 hours, then cooled to ambient temperature. The other slabs were not heated, these slabs being used as controls. Upon completion of the heating, all six slabs were then placed in boiling water with stirring. The control slabs for solutions A, B and C, as well as the heat-treated slabs for solutions A and B underwent substantially complete dissolution in less than 3 minutes, indicating an absence of any substantial amount of crosslinking. The heat-treated slab from solution C remained substantially insoluble after 10 minutes, indicating a substantial degree of crosslinking.

This example shows the need for both sugar and salt in order to effectuate substantial crosslinking.

Example 3

High fructose corn syrup (13.4 parts) and sodium acetate (2.1 parts) were dissolved in water (43 parts). Gelatin (19.2 parts, 80-90 Bloom, Type B) was added, and the solution was heated to 60° C. to dissolve the gelatin. Vitamin A acetate oil (22.3 parts of oil having 2.1 million international units {MIU} per gram) containing ethoxyquin (80 mg/MIU vitamin A) and BHT (10 mg/MIU vitamin A) was added and the resulting mixture was homogenized at 60° C., resulting in an aqueous emulsion with oil droplets approximately 2 microns in diameter.

The emulsion was then spray-congealed using hydrophobic starch as the absorbant. The vitamin-active beadlets were then separated from the excess starch so that a product was obtained in which the beadlets ranged in size between about 105 microns to about 840 microns. The resulting beadlets were dried in a fluid-bed dryer to a moisture of about 6.0 weight percent. The beadlets were then heated to 75° C. for eight hours in the fluid-bed dryer with humidified air so that the moisture of the beadlets was maintained between 6 and 9 weight percent. When the heating was complete, the beadlets were dried to a final moisture content of 4.1%. The final product was substantially crosslinked, being substantially insoluble in boiling water for longer than 15 minutes.

Example 4

Three gelatin solutions were prepared by dissolving gelatin (18.6 parts, 80-90 Bloom Type B), fructose (5.3 parts) and calcium acetate (5.0 parts) in water (50.2 parts) heated at 60° C. Calcium hydroxide was added to each solution (0.15, 0.30 and 0.45 parts, respectively) to adjust the pH (at 60° C.) of the solutions to 7.0, 8.0 and 9.0, respectively.

A slab was prepared for each solution as described in Example 1 (supra). The slabs were then heated at 70° C. for 6 hours. During heating, all three slabs turned color from straw-colored to dark brown. The slabs were then placed in boiling water with stirring. All three slabs were substantially insoluble after 12 minutes, indicating each was slab substantially crosslinked. However, the gelatin matrix integrity appeared to increase with increasing pH.

This example illustrates the effect of pH o the process for producing a crosslinked gelatin matrix.

Example 5

Fructose (3.0 parts), sodium acetate (5.0 parts) and hydrolyzed gelatin (18.6 parts) were dissolved in water (50.2 parts) heated at 60° C. Two slabs were prepared as described in Example 1, supra. One slab was placed in an oven at 70° C. for 6 hours, then cooled to ambient temperature, the other slab was kept as a control. The heated slab turned from straw-colored to dark brown during heating. Both slabs were then placed in boiling water with stirring. The control slab underwent substantially complete dissolution in less than 1 minute, while the heat-treated slab took longer (less than 3 minutes) to completely dissolve.

These results indicate that hydrolyzed gelatin can be crosslinked by the process of the present invention, but not to the same degree as unhydrolyzed gelatin.

Example 6

Fructose (5.2 parts), calcium acetate (4.3 parts), glycerin (2.2 parts) and caramel color (2.4 parts) were dissolved in water (50.3 parts). Gelatin (22.9 parts, 80-90 Bloom Type B) was added and the solution was heated to 60° C. to dissolve the gelatin. Vitamin A acetate oil (24.3 parts of 2.1 MIU/g) containing ethoxyquin (80 mg/MIU vitamin A) and BHT (10 mg/MIU vitamin A) was added, and the resulting mixture was homogenized at 60° C., resulting in an aqueous emulsion with oil droplets approximately 2 microns in diameter.

The emulsion was then spray-congealed using hydrophobic starch as the absorbant. The vitamin-active beadlets were then separated from the excess starch so that a product was obtained in which the beadlets ranged in size between about 105 microns to about 840 microns. The resulting product was dried in a fluid-bed dryer to a moisture of about 8.0 weight percent. The product was then heated in the fluid-bed to 75° C. for 8 hours with hot, humidified air, so that the moisture content of the product was maintained between 6 and 9 weight percent during the course of heating. When the heating was complete, the product was dried to a final moisture content of 4.1%. The final product was substantially crosslinked, being substantially insoluble in boiling water for greater than 15 minutes.

Example 7

Three solutions, A, B, and C, were prepared, each containing
gelatin (18.6 parts, 80-90 Bloom, Type B) dissolved in water (50.2 parts) heated at 60° C. Additionally, solution A contained sodium acetate (5 parts) and sucrose (3 parts), solution B contained calcium acetate (5 parts) and sucrose (3 parts), and solution C contained sucrose (3 parts), but no salt. Slabs were prepared for each solution as described in Example 1 (supra), then heated at 70° C. for 6 hours. No color change was observed during heating for any of the slabs. After cooling to ambient temperature, the slabs were placed in boiling water with stirring. All three slabs underwent substantially complete dissolution in less than 2 minutes, indicating that no substantial crosslinking occurred during heating of any of the slabs.

Example 8

Five solutions were prepared containing sodium acetate (5 parts), gelatin (18.6 parts, 80-90 Bloom, Type B) and water (50.2 parts). Each solution was heated to 60° C. in order to dissolve the gelatin. In addition, each solution contained one of the following sugars: glucose (5.6 parts), mannose (5.6 parts), invert sugar (5.6 parts), corn syrup (4 parts, containing approximately 75 weight percent solids) and high fructose corn syrup (5.6 parts). Slabs were prepared for each solution as described in Example 1 (supra). The five slabs were then heated at 70° C. for 6 hours. The glucose, mannose, invert sugar and high fructose corn syrup slabs all turned dark brown during heating. The corn syrup slab turned amber during heating.

After heating, the slabs were allowed to cool to ambient temperature. The cooled slabs were then placed in boiling water, with stirring. All 5 slabs remained substantially insoluble after at least 5 minutes in boiling water, indicating they were all substantially crosslinked.

Example 9

Three solutions, A, B and C, were prepared by dissolving gelatin (11.4 parts, 80-90 Bloom, Type A) in 88.6 parts water heated to 45°-50° C. Additionally, solutions A and B both contained aluminum subacetate filtrate (ASF) solution (6.58 parts stock solution diluted with 13.16 parts water, prepared fresh as described by Shank in U.S. Pat. No. 4,500,453, column 8, lines 1-67) which was added slowly with vigorous stirring, being careful to maintain the temperature of the gelatin solutions above 35° C. Solution B also contained fructose (2.7 parts). In addition to gelatin and water, solution C also contained undiluted ASF stock solution (18 parts) and fructose (2.7 parts).

Once addition of the ASF solution was complete, two slabs were prepared for each solution as described in Example 1, supra. Then, one slab for each solution was heated at 70° C. for 6 hours, while the other slab was kept as a control. All 3 control slabs were clear and colorless.

After heating, the appearance of slab A remained unchanged, but slabs B and C had darkened. All 6 slabs were then placed in boiling water with stirring. The 3 control slabs underwent substantially complete dissolution in less than 2 minutes. Heat-treated slabs A and B underwent substantially complete dissolution in less than 3 minutes. Heat-treated slab C completely dissolved in less than 4 minutes.

Example 10

Four solutions (A, B, C and D) were prepared, each containing gelatin (18.6 parts, 80-90 Bloom, Type B) and fructose (3 parts) dissolved in water (50.2 parts) which was heated to 60° C. Additionally, solution A contained sodium propionate (3 parts) and glycerin (2.3 parts), solution B contained calcium propionate (3 parts) and glycerin (2.3 parts), solution C contained sodium benzoate (5.0 parts) and solution D contained potassium carbonate (5.0 parts). Slabs were prepared for each solution as described in Example 1, supra and heated at 70° C. for 6 hours. All four slabs turned dark brown during heating. The slabs were then placed into boiling water with stirring. All four slabs remained substantially insoluble after 15 minutes in boiling water, indicating each slab underwent a substantial degree of crosslinking.

Example 11

Gelatin (18.6 parts, 80-90 Bloom Type B), fructose (3.0 parts) and sodium carbonate (5.0 parts) were dissolved in water (50.2 parts) heated at 60° C. Once the gelatin had dissolved, the temperature of the solution was increased to about 75° C., at which point a strong amine odor developed, followed by a rapid increase in viscosity. Within 10 minutes at about 75° C. the solution had set into a gel which was dark amber in color and insoluble in water.

This Example illustrates that the process of the present invention can be carried out using water in an amount of about 60 weight percent, based on the weight of the composition. However, further experiments have revealed that the process can be carried out using water in an amount of about 80 weight percent. Therefore, it is believed that the process can be carried out with a composition comprising water in an amount of as high as about 90 weight percent, based on the weight of the composition.

We claim:

1. A method for crosslinking gelatin, comprising the steps of:
   A. making an aqueous composition of:
      i. a gelation,
      ii. a sugar, wherein the sugar is at least one member selected from the group consisting of fructose and glucose,
      iii. a salt, wherein the salt is at least the member selected from the group consisting of water-soluble salts of carboxylic acids, sodium carbonate, potassium carbonate, calcium sulfate, calcium phosphate,
      iv. water, and
      v. at least one fat-soluble vitamin; and
   B. heating the composition while maintaining the moisture content of the composition at a level of at least 3 weight percent, said heating occurring at a temperature of from about 55 to about 85 degrees C.;

so that the gelation is crosslinked to a degree at which it is substantially water insoluble upon being placed in water at 100° C. for at least 3 minutes.

2. The method of claim 1 wherein said fat-soluble vitamin is vitamin A oil.

3. A method for crosslinking gelation, comprising the steps of:
   A. making an aqueous composition of:
      i. a gelatin,
      ii. a sugar, wherein the sugar is at least one member selected from the group consisting of fructose and glucose,
      iii. a salt, wherein the salt is at least one member selected from the group consisting of sodium acetate, calcium acetate, sodium propionate, calcium propionate, sodium benzoate, sodium carbonate, potassium carbonate, calcium sulfate, calcium phosphate, sodium tartrate, aluminum subacetate and sodium glutarate,
      iv. water;
      v. at least one fat-soluble vitamin; and B. heating the composition while maintaining the moisture content of the composition at a level of from about 90 weight percent to about 3 weight percent, said heating occurring at a temperature of from about 55 to about 85 degrees;

so that the gelation is crosslinked to a degree at which is substantially water insoluble upon being placed in water at 100° C. for at least 3 minutes.

4. A method for crosslinking gelatin, comprising the steps of:
   A. making a composition which is an aqueous solution, wherein the solution comprises:
      i. a gelatin;
      ii. a sugar, wherein the sugar is at least one member selected from the group consisting of fructose and glucose;
      iii. a salt, wherein the salt is at least one member selected from the group consisting of sodium acetate, calcium acetate, sodium propionate, calcium propionate, sodium benzoate, sodium carbonate, potassium carbonate, calcium sulfate, calcium phosphate, aluminum subacetate, sodium tartrate, and sodium glutarate;
      iv. water;
      v. at least one fat-soluble vitamin; and
   B. agitating the solution so that an emulsion is formed;
   C. reducing the water content of the emulsion until the emulsion has a moisture content of from about 15 weight percent to about 4 weight percent;
   D. heating the composition while maintaining the moisture content of the composition at a level of at least 3 weight percent, said heating occurring at a temperature of from about 55 to about 85 degrees C.;

so that the gelation is crosslinked to a degree at which it is substantially water insoluble upon being placed in water at 100° C. for at least 3 minutes.

5. The method of claim 4 wherein said fat-soluble vitamin is vitamin A oil.

6. The method of claim 3 wherein the composition comprises:
   A. the gelatin in an amount of from about 10 weight percent to about 70 weight percent,
   B. the sugar in an amount of from about 3 to about 30 weight percent,
   C. the salt in an amount of from about 0.5 to about 25 weight percent,
   D. the fat-soluble vitamin is vitamin A oil in an amount of from about 0.1 weight percent to about 60 weight percent, and wherein the moisture content of the composition is maintained at from about 3 weight percent to about 90 weight percent.

7. The method of claim 6 wherein the gelatin has a bloom of from about 50 to about 300.

8. The method of claim 6 wherein the heating is carried out for a period of at least 30 seconds.

9. The method of claim 8 wherein said heating occurs at a temperature of about 75 degrees C.

10. The method of claim 6, wherein:
    A. the gelatin has a bloom of from about 50 to about 300, the gelatin being present in an amount of from about 10 weight percent to about 30 weight percent, based upon the weight of the composition;
    B. the sugar is present in an amount of from about 5 weight percent to about 20 weight percent, based upon the weight of the composition;
    C. the salt is present in an amount of from about 1 weight percent to about 10 weight percent, based upon the weight of the composition; and
    D. the vitamin A oil is present in an amount of from about 5 weight percent to about 55 weight percent.

11. A method for crosslinking gelatin, comprising the steps of:
    A. making an aqueous solution of:
       i. a gelatin having a bloom of from about 50 to about 300, the gelatin being present in the composition in an amount of from about 10 weight percent to about 30 weight percent, based on the weight of the composition,
       ii. a sugar, wherein the sugar is at least one member selected from the group consisting of fructose and glucose, the sugar being present in the composition in an amount of from about 3 weight percent to about 30 weight percent, based on the weight of the composition,
       iii. a salt, wherein the salt is at least one member selected from the group consisting of sodium acetate, calcium acetate, sodium propionate, calcium propionate, sodium benzoate, sodium carbonate, and potassium carbonate, wherein the salt is present in an amount of from about 0.5 weight percent to about 25 weight percent, based upon the weight of the composition,
       iv. water in an amount of from about 25 weight percent to about 60 weight percent, based on the weight of the composition, and
       v. vitamin A oil which is present in the composition in an amount of from about 0.1 weight percent to about 60 weight percent, based on the weight of the composition;
    B. gelling the aqueous solution;
    C. reducing the moisture content of the gel to a reduced level of from about 15 to about 3 weight percent;
    D. heating the gel to a temperature of from about 55° C. to about 85° C. for a period of from at least 2 hours to about 20 hours, while maintaining the moisture content of the gel at a level of at least 3 weight percent;

so that the gelatin is crosslinked to a degree at which it is substantially water insoluble upon being placed in water at 100° C. for at least 15 minutes.

12. The method of claim 11, wherein:
    A. the aqueous composition is an emulsion which comprises:
       i. a gelatin having a bloom of about 85, the gelatin being present in an amount of about 17 weight percent, based upon the weight of the composition,
       ii. a sugar, wherein the sugar is high fructose corn syrup, the sugar being present in an amount of about 10 weight percent, based upon the weight of the composition,
       iii. a salt, wherein the salt is sodium acetate, wherein the salt is present in an amount of about 2 weight percent, based upon the weight of the composition,
       iv. water, in an amount of about 48 weight percent, based upon the weight of the composition; and
       v. vitamin A oil in an amount of about 22 weight percent, based upon the weight of the composition, B. the heating is carried out by maintaining the moisture content of the composition at a level of at least about 4 weight percent;

so that the gelatin is crosslinked to a degree at which it is substantially water insoluble upon being placed in water at 100° C. for at least 15 minutes.

13. The method of claim 12 wherein the heating is carried out at a temperature of about 75° C. for a period of about 8 hours.

14. A crosslinked gelatin product, comprising:
A. a gelatin wherein the gelatin is crosslinked to a degree at which it is substantially water insoluble upon being placed in water at 100° C. for at least 3 minutes;
B. a sugar, wherein the sugar is at least one member selected from the group consisting of fructose and glucose;
C. a salt, wherein the salt is at least one member selected from the group consisting of water-soluble salts of carboxylic acids, sodium carbonate, potassium carbonate, calcium sulfate, calcium phosphate;
D. water;
E. at least one fat-soluble vitamin.

15. The product of claim 14 wherein:
A. the gelatin is present in an amount of from about 10 percent to above 70 weight percent, based on the weight of the product,
B. the sugar is present in an amount of from about 3 to about 30 weight percent, based on the weight of the product,
C. the salt is present in an amount of from about 0.5 to about 25 weight percent, based on the weight of the product,
D. the fat-soluble vitamin is vitamin A oil and is present in an amount of from about 0.1 weight percent to about 60 weight percent, based on the weight of the product, and
E. the water is present in an amount of from about 1 weight percent to about 18 weight percent, based on the weight of the product.

16. The product of claim 15 wherein the gelatin has a bloom of from about 50 to about 300.

17. The product of claim 16, wherein:
A. the gelatin has a bloom of from about 50 to about 300, the gelatin being present in an amount of from about 15 weight percent to about 50 weight percent, based upon the weight of the product,
B. the sugar is at least one member selected from the group consisting of fructose and glucose, wherein the sugar is present in an amount of from about 10 weight percent to about 30 weight percent, based upon the weight of the product,
C. the salt is at least one member selected from the group consisting of sodium acetate, calcium acetate, sodium propionate, calcium propionate, sodium benzoate, sodium carbonate, potassium carbonate, calcium sulfate, calcium phosphate, aluminum subacetate, and wherein the salt is present in an amount of from about 2 weight percent to about 10 weight percent, based upon the weight of the product;
D. the water is present in an amount of from about 3 weight percent to about 13 weight percent; and
E. the vitamin A oil is present in an amount of from about 10 weight percent to about 50 weight percent.

18. The product of claim 17, wherein:
A. the gelatin has a bloom of from about 80 to about 90, the gelatin being present in an amount of about 30 weight percent, based upon the weight of the product;
B. the sugar is high fructose corn syrup, the sugar being present in an amount of about 20 weight percent, based upon the weight of the product;
C. the salt is sodium acetate, wherein the salt is present in an amount of about 5 weight percent, based upon the weight of the product;
D. the water is present in an amount of about 4 weight percent, based on the weight of the product; and
E. wherein the vitamin A oil is present in an amount of about 40 weight percent.

19. The product prepared according to the process of claim 3.

* * * * *